United States Patent [19]

Xhajanka

[11] 4,264,592

[45] Apr. 28, 1981

[54] CITRUS FRUIT FRESH CREAM

[76] Inventor: Kosta Xhajanka, c/o John Sargeant, III 92 Maple Ave., Greenwich, Conn. 06830

[21] Appl. No.: 5,452

[22] Filed: Jan. 22, 1979

[51] Int. Cl.$^3$ ............................................. A61K 35/78
[52] U.S. Cl. ..................................... 424/195; 424/49; 424/58; 424/358; 426/616
[58] Field of Search ........................................ 424/195

[56] References Cited

U.S. PATENT DOCUMENTS

| | | | |
|---|---|---|---|
| 3,112,202 | 11/1963 | Wadsworth | 426/616 |
| 3,890,212 | 6/1975 | Harich | 424/195 |

OTHER PUBLICATIONS

Pharmaceutical Formulas, 1954, vol. I 12th edition, pp. 109 to 114, 287, 307, 317, 778 & 779.
The Complete Book of Natural Cosmetics 1974, Traven, pp. 41, 42, 46, 47, 48, and 68.
Harry, Modern Cosmeticology, 1947, pp. 53 & 54.
Handbook of Cosmetic Materials, 1954, pp. 231 & 232, Greenberg, et al.

*Primary Examiner*—Dale R. Ore
*Attorney, Agent, or Firm*—Roger M. Rickert

[57] ABSTRACT

A citrus fruit fresh cream cosmetic manufactured from the solid parts of citrus fruit. By blending and homogenizing, an equal quantity in volume of tenderized solid parts of citrus fruit and fresh drinking water, an emulsion is produced as a colloidal dispersion of all the constituents of the fruit in the fresh water. The citrus fruit fresh cream is a cleanser-emulsion by the action of water reducing its surface tension.

7 Claims, No Drawings

CITRUS FRUIT FRESH CREAM

The present invention relates to mass production of a new and useful product, the citrus fruit fresh cream: Citrus fruit fresh cream is manufactured from the solid parts of citrus fruit such as peel, pulp and rags. These solid parts of citrus fruit are first only tenderized at room temperature by treatment in an aqueous solution. Their natural appearance, structure, aroma, flavor and color are unchanged, sebsequently they are sorted in quantity, quality, variety and stored. By blending and homogenizing, an equal quantity in volume of tenderized solid parts of citrus fruit and fresh drinking water, an emulsion is produced as a colloidal dispersion of all the constituents of the fruit in the fresh water. Water is the continuous phase and all the constituents of the fresh fruit are the disperse phase. The citrus fruit fresh cream is a cleanser-emulsion by the action of water reducing its surface tension. Physical appearance and dispersion are alike the well known whipped creams. Flavor and aroma are characteristic to the flavor and aroma of the fruit such as lemon, orange, lime, grapefruit, tangerine and alike citrus. More particularly this invention relates to the important quality of the citrus fruit fresh cream. It dissolves perfectly in fresh water. Quantities of 1 part of cream to 20 parts or more of water by blending, one produces a variety of concentrations of citrus fruit juice-like products. Fresh citrus fruits have a considerable value in the daily diet of human beings. The large number of chemical constituents and enzymes systems, estimated to a minimum of several hundred, causes the fresh citrus to be one of the most significant natural resources. Citrus fruits are a primary natural source of Vitamin C with small but important amounts of provitamin A, Vitamins B such as Biotin, Folic Acid, Inositol, Niacin, Thiamine, Riboflavin and pantothetic acid. Fresh citrus fruits, in addition, have an important nutritional value by the amino acids, proteins, glucoproteins, inorganic salts, sugars, carbohydrates and other unidentified factors and prosthetic action groups.

The nitrogenous constituents known to occur in citrus fruits include proteins, conjugated proteins, simple peptides, amino acids, betaines, phosphotides, and related substances.

The proteins in citrus fruit are insoluble in general and are found to be associated, in particular, with the solid parts of the fruit such as the peel—flavedo, albedo, chromatophores, flavonoids,—and pulp.

In the solid parts of the citrus fruit are also included the major part of carbohydrates such as the polysaccharides and pectin, the flavornoid glucosides, the pigments, the lipid fatty acids and citrus fruit aromatic oils. The citrus industry in U.S.A. only, is processing about 200 millions of citrus fruit boxes per year. Each box of 90 pounds yields 1.30 gallons of juice, approximately 10 percent of the whole fruit weight. As a result the solid parts of the fruit, peel, pulp and rangs constitute an immense amount of valuable material. From a large quantity of this huge amount is extracted the citrus pectin as a byproduct and from an insignificant quantity is expressed the orange peel oil. The remainder is considered an cannery waste and is transformed expensively and laboriously in feed product and fertilizer. The manufacure of pectin is a very expensive and complicated process of chemical extraction. It is composed of various and numerous batch type operations with corrosive chemicals such as acids and alkalis and very expensive organic solvents. Shredding, filtrations, neutralizations, purifications and vacuum drying operations are done at 80° C. temperature. In addition, the extraction is limited to a low yield. It is estimated that two million tons of citrus peel yield about only 2.5 thousand tons of citrus pectin.

The citrus processing industry in manufacturing canned or fresh citrus juices, is deeply concerned to the enormous depreciation and loss of the solid parts of the fruit. These immense amount of cannery waste present also a serious disposal problem and therefrom other important expenses are added to maintain the ecological regulations and restrictions of pollution control. It has been a long sought objective in citrus economy that continual attention must be given to new technologies in the utilization and processing of citrus fruit other than for the fresh fruit market, in order to effectively market the ever expanding production of citrus fruits. It is imperative to the national economy to utilize rationally to the maximum the whole citrus fruit.

The primary object of the present invention is to provide a simple and inexpensive method of producing from only the solid parts of the fruit unlimited quantities of citrus fruit fresh cream and therefrom citrus juice—like products. Still another important object is to furnish to the scientific community aqueous solutions of the solid parts of fruit in order to provide easy way and first step, at room temperature, for complete biochemical analysis of all the chemical constituents of the fruit which are estimated to a minimum of several hundred. Another object is to supply aqueous solutions of the fruits therefore eliminating the prior selective extractions which are expensive, time consuming and difficult to define. The new techniques of filter paper chromatography and adsorption, ion-exchange and partition, for qualitative and quantitative estimations and analysis of the constituents of citrus fruit, can be largely helped and less expensive by the provision of such aqueous solutions. A further important object of the invention is to provide such a large quality of aqueous solutions of the solid parts of the fruit that any important chemical constituent with potential, nutrition, health, medical and other biological values can be discovered, extracted and produced less expensively from these aqueous solutions which are the ideal media of operations such as: fractionations, separations, purifications, isolations, etc. Another object of this invention is to provide such aqueous solutions as a first step in advanced research of molecular biochemistry in order to discover in the solid parts of citrus fruit new molecular structures and new biological functions between free sugars, polysaccharides, proteins, glucoproteins, glucolipids, and flavonoid glucosides. From important economical considerations another primary object of this invention is to provide the mass production of citrus fruit fresh cream for manufacturing inexpensive by-products existant or new and in addition to supply a novel basic product with unlimited marking potentials in medical, pharmaceutical, drug, and cosmetic industries.

From immediate practical needs another very important object of my invention is to provide a new product the citrus fruit fresh cream with a multitude of uses in: 1. Medicine, by the action of flavonoid glucosides as an antibacterial, antiviral and the so-called vitamin P which promote the tensile strength on capillary walls; By the action of the active pectin as an hemostatic agent healing deep wounds, plasma substitute and to lower cholesterol; By the action of pigments which are related to carotenoids—chlorophyll—and especially to b—carotene as a provitamin A to promote the epithelium tissues; 2. Cosmetics, as a cleanser-emulsion water vanishing toothpaste, mouthwash antiseptic against periodontal disease, plaques, dental caries and by the effective inhibition action in the development of mouth flora.

Citrus fruit fresh cream in aqueous solution is cationic and strongly antioxidant. It neutralizes soaps, detergents, bleach and ammonia by the action of active protons. In aqueous solution the complex buffered mixture has a pH of about 4 to 4.5.

Some practical properties of citrus fruit fresh cream are: Free air exposure at room temperature in small quantities around 2 in × 2 in × 2 in makes it dry without deterioration. For large quantities in the jar after 30 days exposure in free air only a light off-flavor takes place by the action of oxygen on pectin. Refrigerated around $-5°$ C. to $0°$ C. is preserved in flavor, aroma and freshness per years.

The citrus fruit fresh cream is an emulsion as a colloidal dispersion of all the chemical constitutents of the fruit in the fresh water. Water is the continuous phase and all the chemical constitutents of the fresh fruit are the disperse phase. The surface tension of water is reduced.

Considering that the overall chemical constituents of citrus fruit are estimated to a minimum of several hundred and their colloidal dispersion in the fresh water, the action of citrus fruit fresh cream as a nature's drug should be imperative in large number of diseases and in particular in experiments related to stomach and colon cancer.

The established effectiveness as antibacterial and antiviral and the slow action as antioxidant by the active proton release is largely encouraging for more examinations and tests with citrus fruit fresh cream.

The citrus fruit fresh cream is a basic product and a new approach beneficial to the health of human beings and national economy.

THE METHOD OF TENDERIZING THE SOLID PARTS OF CITRUS FRUIT

I have found a method to tenderize the solid parts of the citrus fruit by treating ten in an aqueous solution. The aqueous solution is prepared from the following ingredients.

(1) Sulfuric acid 95 percent, pure with lead content maximum of 0.00001 percent; (2) sodium persulfate; (3) Solution of 50 grams of solution persulfate in one liter of sulfuric acid; (4) Fresh orange fruit peels ground and dehydrated at vacuum to about 30 percent water content; (5) Aluminum zinc sulfate; (6) Sodium acid pyrophosphate. The process of preparation of aqueous solution involves: In one liter of fresh water, add 5 milliliters from solution (3); to this solution add 20 grams of ingredient (4); 5 grams of ingredient (5); and 5 grams of ingredient (6); Stir thoroughly this aqueous solution for complete mixing of ingredients at room temperature. Let settle during two hours at pH between 2 and 2.5. For one liter of aqueous solution to 0.2 Kg of solid parts of citrus fruit, the action of tenderizing is maintained to last about 5 hours, for the oranges, and grapefruit. For lemon about 6 hours and for lime 7 hours. The immersion is done in large tanks by holding the solid parts all together as they are without other preparation. Ingredients, proportions and time are established to produce tenderized solid parts of citrus fruit to withstand and support thoroughly washing and preserve their structure, aroma, flavor and color. Their natural appearance is unchanged- subsequently the solid parts after tenderizing are taken out and thoroughly washed with fresh water to drain out any drop from the aqueous solution. Subsequent washing with fresh water are repeated in sifting tank until any drop of water is drained out.

At this stage the solid parts of citrus fruit are let to dry from the excess water at room temperature for about 5 hours. Subsequently, they are sorted in quantity, quality, variety and stored in plastic bags to avoid excess drying. If the storage is lasting more than 2 hours, in order to preserve freshness and aroma is better to store the bags in the refrigerator for further use. The production of citrus fruit fresh cream is processed by blending; an equal quantity in volume of tenderized solid parts of citrus peel and fresh drinking water are blended together—while the tenderized solid parts of citrus fruit are grinding they absorb water and become more and more hydrated. During the homogenizing processing the water reduces its surface tension and is completely absorbed by the colloidal dispersion when the emulsion is completed. At this point the viscosity of the emulsion is at maximum and the action of blender slows down and may stop. To perform complete homogenizing and avoid heating, is of good advice to blend and mix the emulsion in order to unify the partition of water and tenderized solid parts of citrus fruit. The best results are performed by special chemical blending apparatus used to homogenize rapidly chemical emulsions of high viscosity.

The citrus fruit fresh cream has the physical properties of an emulsion. It constitutes a colloidal dispersion of all the chemical constitutents of the citrus fruit fresh in the fresh water. Water is the continuous phase and all the chemical constituents of citrus fresh fruit are the disperse phase. The citrus fruit fresh cream has more or less emulsifying action by reducing the surface tension of the water. It dissolves by stirring and blending in fresh water. Quantities of 1 part of cream to 20 parts or more of fresh water, by blending, one produces a variety of concentrations of citrus fruit juice—like products. Although preferred embodiments of the invention have been described in details, it is to be understood that various changes, and substitutions, and alterations can be made therein without departing from the spirit and scope of the invention by the appended claims.

What is claimed:

1. A fresh citrus fruit cosmetic cream product obtained by:
   tenderizing fresh orange peel by immersing the peel in an acidic aqueous solution of sulphuric acid, sodium persulfate, aluminum zinc sulfate, and sodium acid pyrophosphate having a pH of about 2.0 to 2.5 for a period of about 5 to 7 hours;
   removing the tenderized peel from the solution;
   rinsing thoroughly with water the removed tenderized peel to remove substantially all trace of the acidic solution;
   mixing substantially equal parts by volume of water and rinsed peel; and
   blending the water—peel mixture to form a homogeneous colloidal dispersion of a fresh citrus fruit cosmetic cream.

2. The fresh citrus fruit cosmetic cream of claim 1 wherein the step of tenderizing is effected in the proportion of about 200 grams of peel per liter of acidic solution, the solution comprising, per liter, about 5 grams of aluminum zinc sulfate, 5 grams of sodium acid pyrophosphate, 5 millilters of sulfuric acid, and 0.25 grams sodium persulfate.

3. The fresh citrus fruit cosmetic cream of claim 2 wherein each liter of the acidic solution further includes about 20 grams of fresh orange peel, ground and dehydrated to about 30 percent water content.

4. The fresh citrus fruit cosmetic cream of claim 3 wherein the acidic solution is mixed and allowed to settle for about 2 hours prior to immersion of the peel.

5. The method of producing a fresh citrus fruit cosmetic cream product comprising the steps of:
   tenderizing fresh orange peel by immersing the peel in an acidic aqueous solution having a pH of about 2.0 to 2.5 for a period of about 5 to 7 hours;
   removing the tenderized peel from the solution;
   rinsing thoroughly the removed tenderized peel to remove substantially all trace of the acidic solution;
   mixing substantially equal parts by volume of water and rinsed peel; and
   blending the water—peel mixture to form a homogeneous colloidal dispersion of fresh citrus fruit cosmetic cream.

6. The method of claim 5 wherein the step of tenderizing includes premixing the acidic solution to contain sulfuric acid, sodium persulfate, aluminum zinc sulfate, sodium acid pyrophosphate, and ground dehydrated orange peel.

7. The method of claim 6 wherein the step of tenderizing further includes allowing the premixed acidic solution to settle for about two hours prior to immersing the peel therein.

* * * * *